(12) United States Patent
Park

(10) Patent No.: US 6,576,190 B1
(45) Date of Patent: Jun. 10, 2003

(54) METHOD AND APPARATUS FOR STERILIZING AND DISINFECTING BEDCLOTHES USING ULTRAVIOLET RAYS AND OZONE

(75) Inventor: Han Oh Park, Choongcheongbuk-do (KR)

(73) Assignee: Bioneer Corporation, Choongcheongbuk-do (KR)

( * ) Notice: Subject to any disclaimer, the term of this patent is extended or adjusted under 35 U.S.C. 154(b) by 0 days.

(21) Appl. No.: 09/869,556

(22) PCT Filed: Sep. 29, 2000

(86) PCT No.: PCT/KR00/01085
§ 371 (c)(1),
(2), (4) Date: Aug. 21, 2001

(87) PCT Pub. No.: WO01/30400
PCT Pub. Date: May 3, 2001

(30) Foreign Application Priority Data

Oct. 29, 1999 (KR) .......................................... 1999/47553

(51) Int. Cl.⁷ .............................. A61L 2/00; A61L 9/00; A62B 7/08; G01N 23/00
(52) U.S. Cl. .............................. 422/28; 422/29; 422/24; 422/32; 422/121; 422/186.03; 422/305; 250/455.1; 250/504 R
(58) Field of Search .......................... 422/1, 4, 22–24, 422/28, 120–121, 123, 186.03–186.23, 186.3, 187, 292, 294–297, 300, 305–306, 906–907; 250/455.1, 504 R

(56) References Cited

U.S. PATENT DOCUMENTS

| | | | | |
|---|---|---|---|---|
| 3,877,152 A | * | 4/1975 | Gorman | |
| 4,700,418 A | | 10/1987 | Ritter | ............................. 5/449 |
| 5,503,808 A | * | 4/1996 | Garbutt et al. | |
| 5,540,978 A | * | 7/1996 | Schrenk | |
| 5,713,137 A | * | 2/1998 | Fujita | |
| 5,868,999 A | | 2/1999 | Karlson | ........................ 422/30 |

FOREIGN PATENT DOCUMENTS

| | | |
|---|---|---|
| JP | 2-088066 | 3/1990 |
| JP | 3-12105 | 1/1991 |
| JP | 3-215265 | 9/1991 |
| JP | 10-314289 | 12/1998 |

OTHER PUBLICATIONS

International Search Report for Application No. PCT/KR00/01085.

Co–pending Application No. 09/869,555, Inventor: Han Oh Park, filed Jun. 29, 2001.

* cited by examiner

Primary Examiner—Robert J. Warden, Sr.
Assistant Examiner—Monzer R. Chorbaji
(74) Attorney, Agent, or Firm—Hunton & Williams

(57) ABSTRACT

A method and apparatus for sterilizing and disinfecting bedclothes. The method includes preparing a sterilizing room defined by a cover; placing bedclothes into the sterilizing room; and exposing the bedclothes to ultraviolet rays and ozone generated by a generator in communication with the sterilizing room. The apparatus includes a generator for generating ultraviolet rays and ozone and a cover for defining a sterilizing room to accommodate the bedclothes.

14 Claims, 6 Drawing Sheets

METHOD AND APPARATUS FOR STERILIZING AND DISINFECTING BEDCLOTHES USING ULTRAVIOLET RAYS AND OZONE

TECHNICAL FIELD

The present invention relates to a method and an apparatus for sterilizing and disinfecting bedclothes, such as a mattress for bed, a coverlet, an oriental mattress, a pillow, etc.

BACKGROUND ART

Generally, bedclothes are articles for daily use, which keep in touch with people every day. The bedclothes are contaminated by sweat, horny substance of a skin, dandruff, hair secreted or separated from the body of the people. Accordingly, harmful microorganisms or noxious insects, such as a mite inhabit the bedclothes to threaten people's sanitation.

In particular, an apartment house in which a lot of people are lived at present is a place where a great number of harmful bacteria and harmful insects are lived since the temperature and the humidity are maintained constantly in the apartment house.

For these reasons, disease, such as allergic rhinitis, allergic asthma, atopic dermatitis, conjunctivitis, etc., become increased suddenly recently.

The harmful bacteria and the harmful insects which cause occurrence of the disease as mentioned above may be exterminated by sterilization and disinfection of the bedclothes. In the home, a pillow, a coverlet, etc., which are movable freely as it are light and small in size, are exposed to the sun for a long time in order to sterilize and disinfect the bedclothes.

However, it is difficult to expose to the sun the bedclothes, such as a mattress for bed, because they are heavy and large in size.

Especially, modern people who are harassed with burdensome business matters cannot afford to transport and expose the bedclothes to the sun for a long time.

Accordingly, it is required to provide a method and apparatus for sterilizing and disinfecting the bedclothes with ease when people have time to spare.

DISCLOSURE OF THE INVENTION

It is an object of the present invention to provide a method and an apparatus for sterilizing and disinfecting bedclothes, such as a mattress for bed, a coverlet, an oriental mattress, a pillow, etc., using ultraviolet rays and ozone.

It is a further object of the present invention to provide an apparatus for sterilizing and disinfecting bedclothes constructed in a foldable type such that it is folded in storage and it is unfolded in use.

It is a still further object of the present invention to provide an apparatus for sterilizing and disinfecting bedclothes which is easy to carry and handle the apparatus and convenient to use it at home.

The foregoing object is accomplished in one embodiment by providing a method and an apparatus for sterilizing and disinfecting bedclothes characterized in that a sterilizing and disinfecting room is prepared by simple development of the apparatus in a portion of the interior of the room or on a mattress for bed, the bedclothes are placed in the sterilizing and disinfecting room, a generator for generating ultraviolet rays and ozone mounted in the sterilizing and disinfecting room is operated, the bedclothes are exposed to the ultraviolet rays and ozone generated by the generator for generating ultraviolet rays and ozone for a predetermined time period to sterilize and disinfect the bedclothes.

BRIEF DESCRIPTION OF THE DRAWINGS

The preferred embodiment of the present invention will now be described by way of example with reference to the accompanying drawings in which.

BEST MODE FOR CARRYING OUT THE INVENTION

Figure 1:
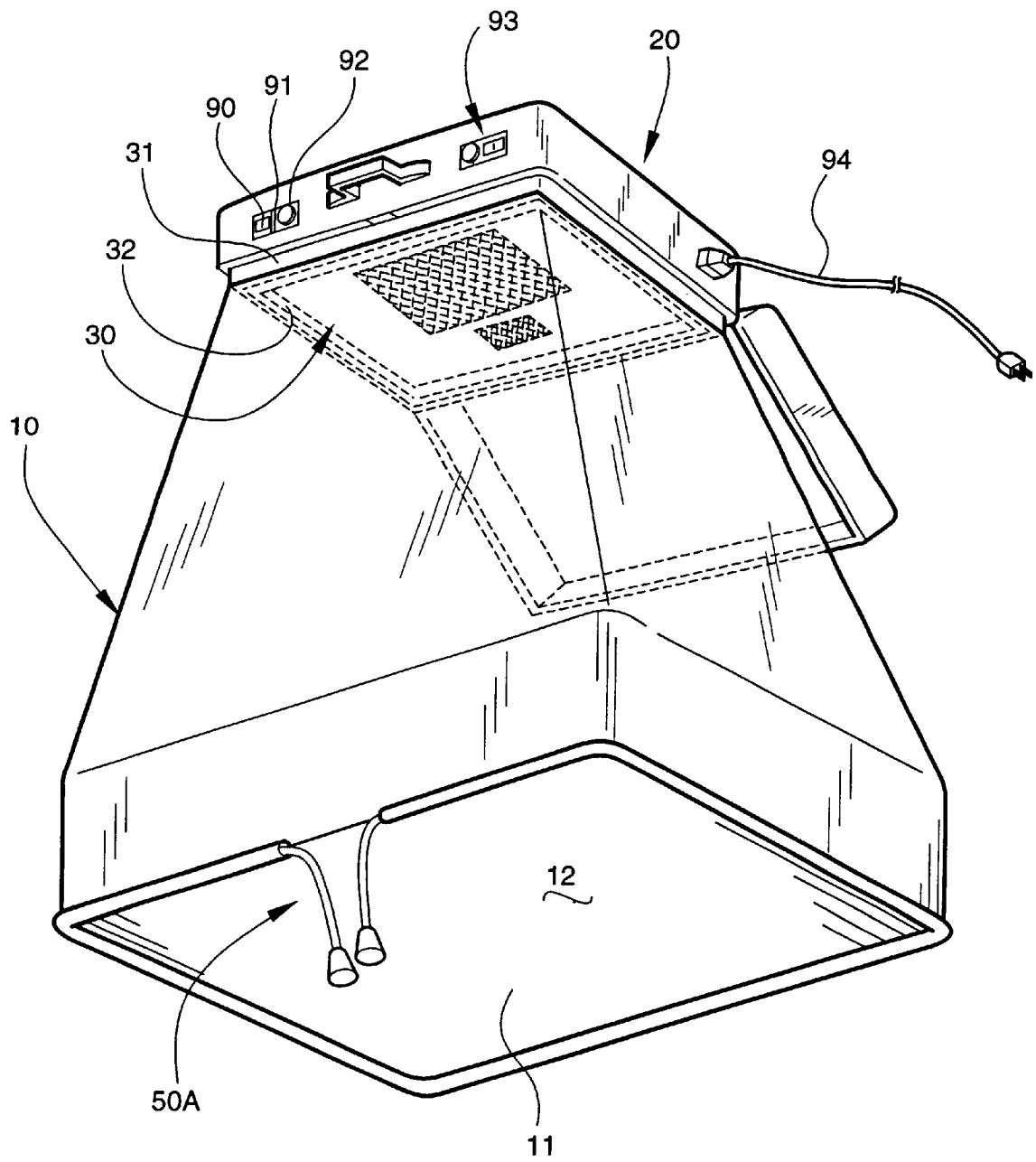
FIG. 1 is a developed perspective view showing the entire structure of an apparatus for sterilizing and disinfecting bedclothes using ultraviolet rays and ozone according to the present invention.

The present invention will be now described in detail.

The bedclothes in which the harmful bacteria and the harmful insects are lived to contaminate the bedclothes as they are used for a long time are isolated for the purpose of sterilizing and disinfecting the bedclothes.

How to sterilize and disinfect the bedclothes are as follows: For sterilization and disinfection of bedclothes, such as a mattress for bed, a folded cover is developed directly on the bedclothes to prepare a sterilizing and disinfecting room in which the bedclothes are isolated. For sterilization and disinfection of bedclothes, such as a coverlet, an oriental mattress, a pillow, etc., the bedclothes are placed in the prearranged sterilizing and disinfecting room, which is arranged in advance regardless of whether the bedclothes are prepared or not. Thereafter, a generator for generating ultraviolet rays and ozone mounted in the sterilizing and disinfecting room is operated. The bedclothes are exposed to the ultraviolet rays and ozone generated by the generator for generating ultraviolet rays and ozone for a predetermined time period to sterilize and disinfect the bedclothes.

In this case, it is preferable that the concentration of the ozone in the sterilizing and disinfecting room is set to 50–90 ppm, the range of the ultraviolet rays is set to 184.9–253.7 nm, and the time of exposure is set to approximately 1–2 hours. The concentration of the ozone, the range of the ultraviolet rays, and the time of exposure vary depending upon the level of contamination of the bedclothes in order that the bedclothes are sterilized and disinfected thoroughly.

The apparatus for embodying the method for sterilizing and disinfecting bedclothes according to the present invention will now be described in detail with reference to the accompanying drawings.

The apparatus for sterilizing and disinfecting bedclothes according to the present invention comprises a cover 10 and a generator 20 mounted in the cover 10 for generating ultraviolet rays and ozone. The cover 10 includes an open area 11 with means for opening and closing the open area 11. The cover 10 is made of foldable material, such as plastic film, waterproof fabric sheet. The cover 10 may include a foldable-coated-fabric sheet. When the cover 10 is developed, the cover 10 defines therein a sterilizing and disinfecting room 12 in which the bedclothes to be sterilized and disinfected are placed in isolated state.

The generator 20 for generating ultraviolet rays and ozone used in the preferred embodiment of the present invention mainly comprises an UV/O3 lamp (184.9–253.7 nm). Alternatively, an arc discharged generator for generating ultraviolet rays and ozone or an air-cooled generator for generating ultraviolet rays and ozone may be used.

The generator 20 for generating ultraviolet rays and ozone includes a fan 80 for flowing the ozone and means for storing the cover 10 by which it is convenient to handle and maintain the apparatus for sterilizing and disinfecting bedclothes according to the present invention.

Figure 2:
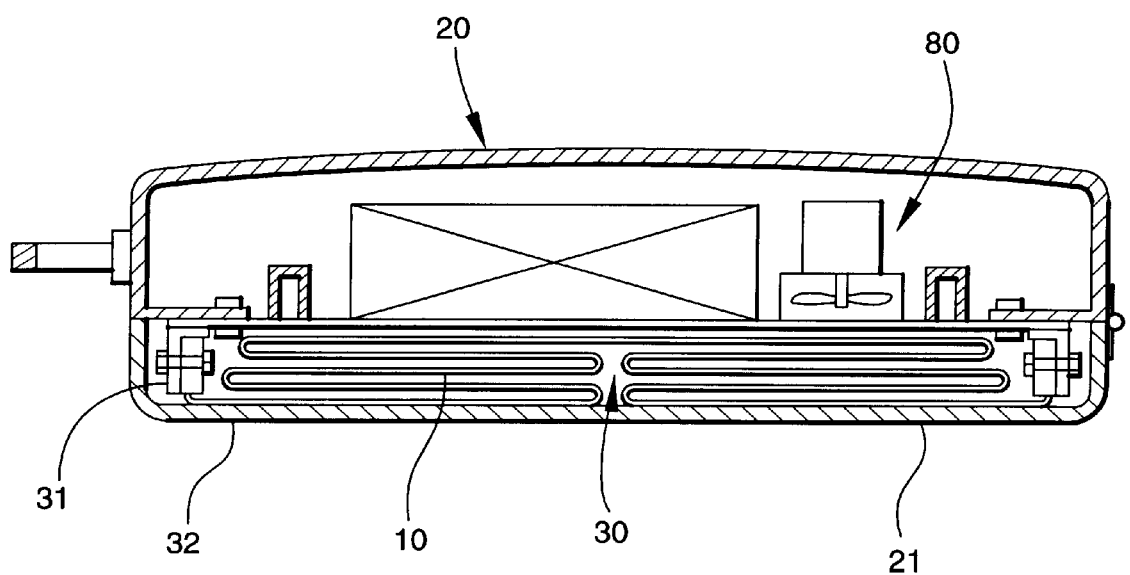
FIG. 2 is an illustrative cross-sectional view showing the apparatus for sterilizing and disinfecting bedclothes using ultraviolet rays and ozone according to the present invention, in the folded state.
Figure 3:
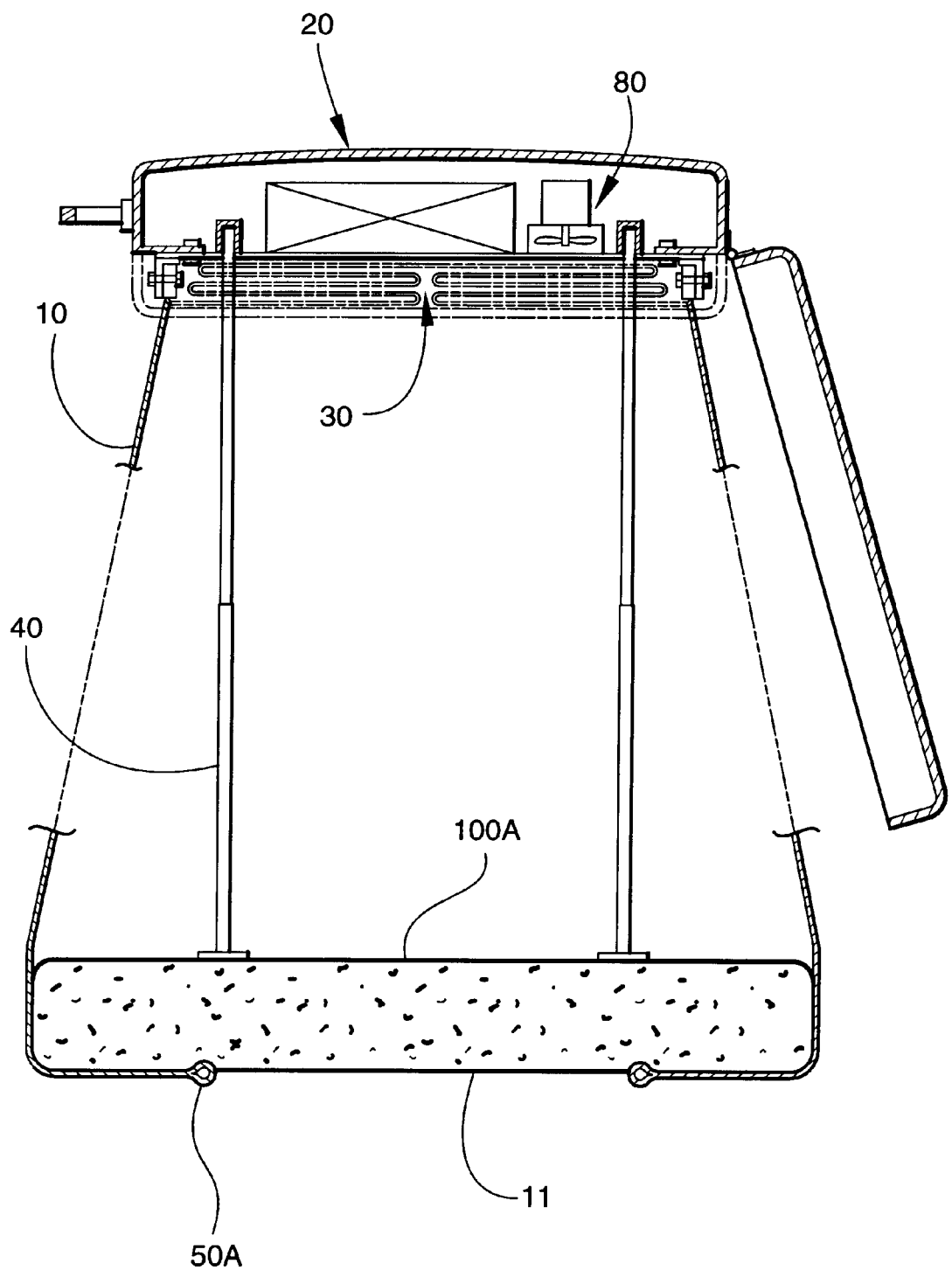
FIG. 3 is an illustrative cross-sectional view showing the apparatus for sterilizing and disinfecting bedclothes using ultraviolet rays and ozone according to the present invention, in the unfolded state.
Figure 4:
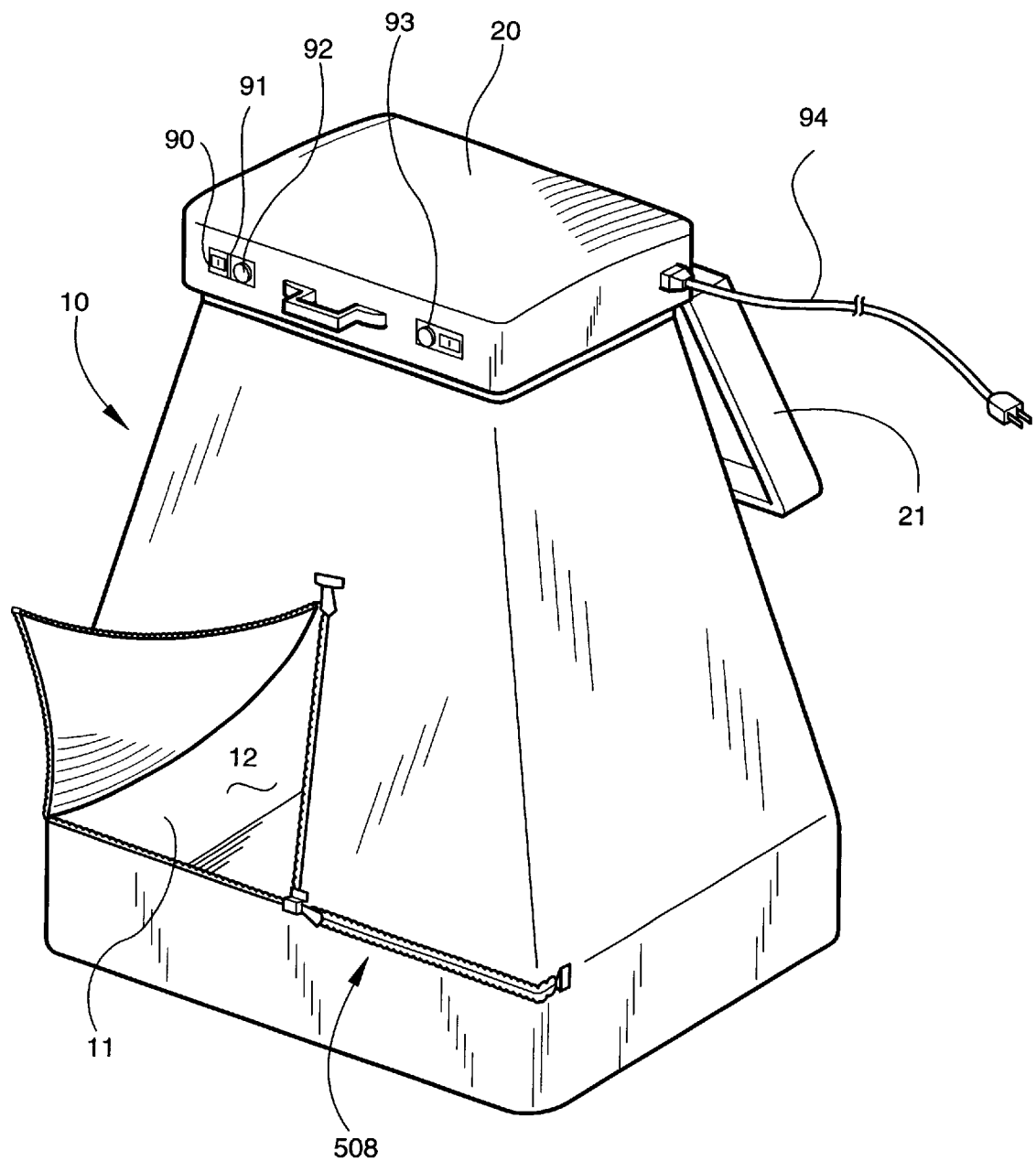
FIG. 4 is a developed perspective view showing another embodiment of the apparatus for sterilizing and disinfecting bedclothes using ultraviolet rays and ozone according to the present invention.
Figure 5:
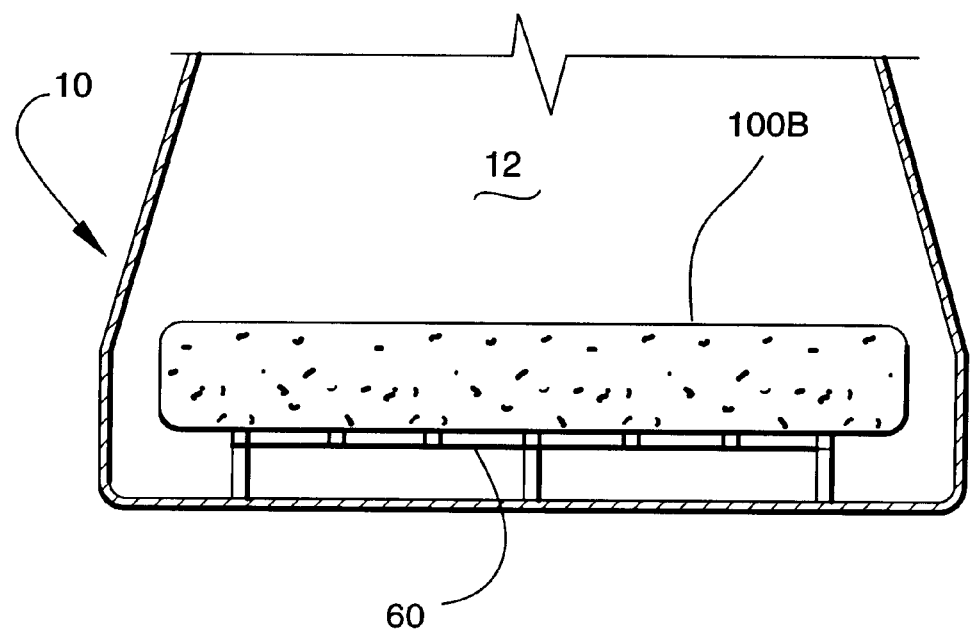
FIG. 5 is an illustrative cross-sectional view showing the apparatus for sterilizing and disinfecting bedclothes using ultraviolet rays and ozone according to the present invention in which a support for bedclothes is arranged.

As shown in FIG. 2 and FIG. 3, the means for storing the cover 10 includes a compartment 30 which is arranged under the generator 20 for generating ultraviolet rays and ozone and which is defined by a lid 21 of the generator 20 for generating ultraviolet rays and ozone. The compartment 30 includes a circumferential wall 31 to which the upper end of the cover 10 is attached, and a fitting member 32 mounted to the inside of the circumferential wall 31 such that the upper end of the cover 10 is sandwiched between the circumferential wall 31 and the fitting member 32.

The cover 10 attached as mentioned above may be folded so that the cover 10 is accommodated in the compartment 30 for the cover 10. And the cover 10 may be closed by the lid 21 of the generator 20 for generating ultraviolet rays and ozone so that it may be easy and convenient to store and carry the apparatus for sterilizing and disinfecting the bedclothes according to the present invention. In use, the lid 21 is opened so that the cover 10 is developed to prepare the sterilizing and disinfecting room 12.

At this time, as shown in FIG. 3, the generator 20 for generating ultraviolet rays and ozone is provided with a stay 40 for maintaining the space of the inside of the sterilizing and disinfecting room 12. Preferably, the stay 40 can be expanded or contracted as a telescopic member.

The means for opening and closing the open area 11 of the cover 10 constructed as mentioned above may be a fastening string 50A which is arranged in the lower end of the cover 10, as shown in FIG. 3.

The mattress 100A for the bed may be introduced into the cover 10 through the open area 11. The fastening operation of the fastening string 50A causes the open area 11 to be closed so that the mattress for the bed may be isolated in the cover 10, and accordingly it is subject to the conditions appropriate for sterilization and disinfection.

Alternatively, the means for opening and closing the open area 11 of the cover 10 may be a zipper 50B of ⊥ shape arranged on the lower portion of the cover 10.

The means for opening and closing the open area 11 of the cover 10 may also be constructed in the form of a magic tape.

In this case, the open area 11 may be zipped so that the bedclothes to be sterilized and disinfected which can be carried easily, such as the coverlet, the oriental mattress, the pillow, etc., are accommodated in the cover 10.

Figure 6:
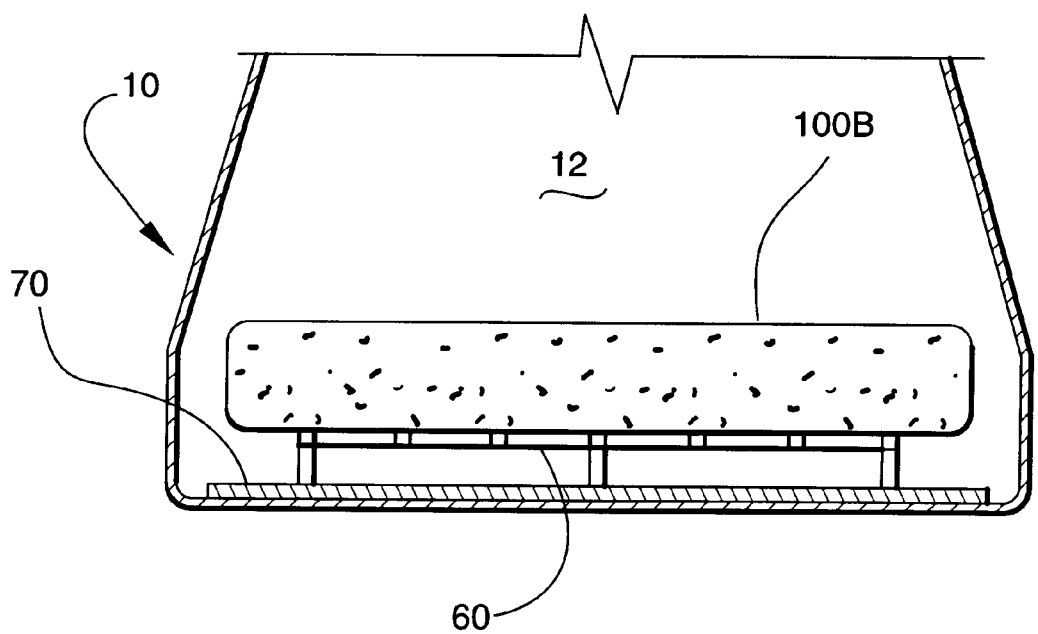
FIG. 6 is an illustrative cross-sectional view showing the apparatus for sterilizing and disinfecting bedclothes using ultraviolet rays and ozone according to the present invention in which a support for bedclothes and a reflection mirror are arranged.

In the interior of the sterilizing and disinfecting room 12 prepared by the development of the cover 10 as mentioned above is provided a support 60 for the bedclothes which is formed to be well ventilated in every directions as shown in FIG. 6. When the bedclothes are placed on the support 60 for the bedclothes constructed as mentioned above, the ozone may apply to the entire bedclothes to accomplish good sterilization and disinfection of the bedclothes. In addition, the support 60 for the bedclothes may be provided with a reflection mirror 70 which is used to irradiate the ultraviolet rays effectively to the entire bedclothes so that better sterilization and disinfection of the bedclothes is accomplished.

In the embodiment as mentioned above, the generator 20 for generating ultraviolet rays and ozone includes a fan 80 for flowing the ozone by which the ozone may be circulated in the sterilizing and disinfecting room 12 so that the bedclothes are exposed to the ozone effectively, a timer 93 which is used to set up the time for sterilization and disinfection, a power switch 90, a fan switch 91, a lamp 90 for indicating the operation, and a cord 94.

As mentioned above, the cover 10 is folded so that the cover 10 is accommodated in the compartment 30 for the cover 10. And the cover 10 is closed by the lid 21 of the generator 20 for generating ultraviolet rays and ozone so that it is easy and convenient to store and carry the apparatus for sterilizing and disinfecting the bedclothes according to the present invention. In use, the lid 21 is opened so that the cover 10 is developed to prepare the sterilizing and disinfecting room 12.

At this time, the interior space in the sterilizing and disinfecting room 12 is maintained by means of the stay 40 which is provided with the generator 20 for generating ultraviolet rays and ozone, and the open area 11 is closed by means of the means for opening and closing the open area 11.

After the installation of the apparatus for sterilizing and disinfecting bedclothes according to the present invention, the time for sterilization and disinfection is set up by means of the timer 93, the generator 20 for generating ultraviolet rays and ozone is operated by means of the power switch 90 to generate the ultraviolet rays and the ozone, the fan 80 for flowing the ozone is driven by means of the fan switch 91 to circulate the ozone in the sterilizing and disinfecting room 12 so that the bedclothes are exposed to the ultraviolet rays and the ozone generated by the generator 20 for generating ultraviolet rays and ozone in order to sterilizing and disinfecting the bedclothes.

Experimental Example 1: Test for Sterilizing Microorganisms

The microorganisms used for the sterilization test were *Escherichia coli* DH12S, *Staphylococcus aureus* KCTC 1621 and Candida albicans KCTC 7965, which are known as pathogenic microorganisms. An UV/O3 lamp (184:9 nm) was used as the generator for generating ultraviolet rays and ozone.

Each of the microorganisms was cultivated on appropriate culture medium used commonly: *Escherichia coli* was cultivated on LB culture medium, *Staphylococcus aureus* was cultivated on Tryptic Soy culture medium; and *Candida albicans* was cultivated on YM culture medium. A sample of the microorganism was prepared as follows: After each of the microorganisms was cultivated on agar culture medium, one colony was taken. And then the colony was inoculated into broths of 5 ml, which was cultivated for two hours. The sample prepared as mentioned above was kept in cold storage for the following use. The broths used for cultivation were diluted gradually from an undiluted solution to 10-8, and then they were painted over the agar culture medium. One control was obtained from each of the diluted samples, and seven samples for test were obtained from each of the diluted samples. The control and samples were subject to pre-incubation in the incubator with the temperature of 37° C. for 30 minutes, which was used for sterilization test.

The concentration of the ozone in the sterilizing and disinfecting room reached 50 ppm within two or three minutes. And the concentration of the ozone was adjusted so that it was maintained to 70 ppm.

Figure 7:
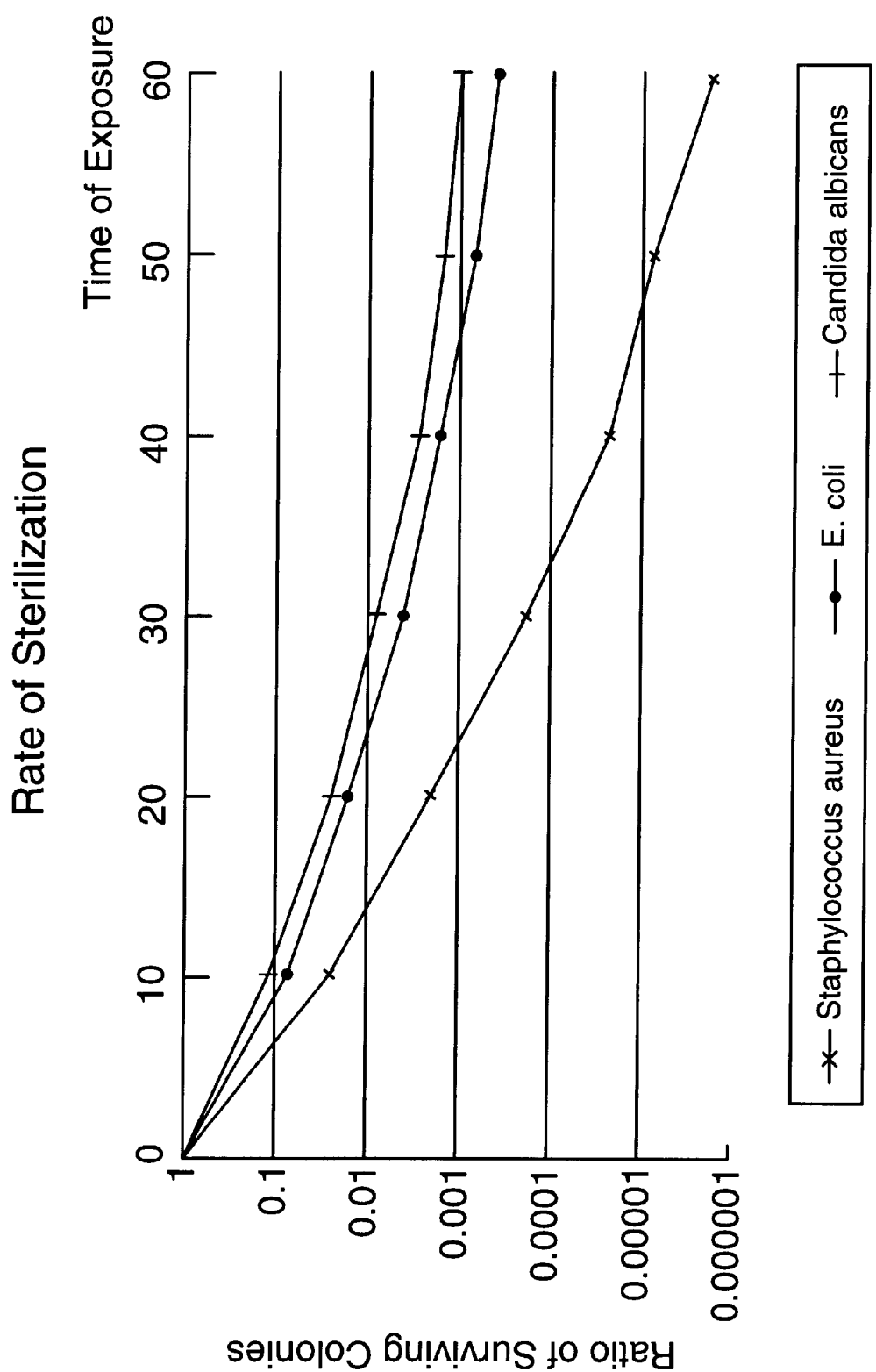
FIG. 7 is a graph showing the relations between rate of sterilization and ratio of surviving colonies obtained from the sterilization of a microorganism according to the present invention.

The humidity was maintained to 50%. The agar culture medium was placed on several position where it was not exposed to the ultraviolet rays and it had good ventilation. One agar culture medium corresponding to the bedclothes as a test sample was taken every ten minutes after the generator for generating the ultraviolet rays and the ozone was operated. The agar culture medium was cultivated together with the control sample in the incubator with the temperature of 37° C. for 48 hours. And then the culture medium diluted such that it had a appropriate number of the colony to check the number of the microorganisms, from which the number of the colony was counted. The number of the real microorganisms and the number of the surviving microorganisms were added together taking the number of the colony and the dilution rate of each sample into account. The test as mentioned above was repeated three times for the purpose of obtaining the statistical effectiveness. The results are shown in Table 1 and FIG. 7.

the number of the surviving mites and the number of the dead mites were counted by means of a microscopic examination. The examination revealed that most of the mites (for example, seventeen mites) were killed. Especially, all of the young mites were killed, and a few surviving large mites were not able to be active normally, which were dead as times went by.

INDUSTRIAL APPLICABILITY

The method for sterilizing and disinfecting the bedclothes according to the present invention as described in detail above is used to expose the contaminated bedclothes to the ultraviolet ray and the ozone so that the bedclothes can be sterilized and disinfected by the ultraviolet ray and the ozone. Therefore, the sterilization and disinfection of the bedclothes is very convenient, and the effect of the sterilization and disinfection is satisfactory. In addition, any harmful substance is not left in the bedclothes because the used ozone can be dissolved easily and simply in the air.

Furthermore, it is easy to carry and handle the apparatus for sterilizing and disinfecting bedclothes according to the present invention, and it is possible to sterilize and disinfect the bedclothes with ease when people have time to spare, because the apparatus of the present invention is constructed in a foldable type such that it is folded in storage and it is unfolded in use.

What is claimed is:

1. A method comprising the steps of: preparing a sterilizing and disinfecting room using a sterilizing and disinfecting apparatus comprising a foldable cover attached to a compartment, the foldable cover being supportable by a stay for maintaining an interior space within the foldable cover; placing bedclothes in the sterilizing and disinfecting room; and exposing the bedclothes to ultraviolet rays and ozone.

2. The method as claimed in claim 1, wherein the sterilizing and disinfecting apparatus comprises an ultraviolet ray and ozone generator, the ultraviolet ray and ozone generator being used in the step of exposing the bedclothes to ultraviolet rays and ozone.

3. The method of claim 1, wherein the step of preparing a sterilizing and disinfecting room comprises developing the

TABLE 1

| Surviving | Number of surviving microorganisms in ozone of 70 ppm |||||||
|---|---|---|---|---|---|---|---|
| | Time of exposure |||||||
| colonies | 0 min. | 10 min. | 20 min. | 30 min. | 40 min. | 50 min. | 60 min. |
| S. aureus | 46,700,000 | 1,220,000 | 101,000 | 9,100 | 1,260 | 345 | 96 |
| | | (±92,000) | (±14,000) | (±1,200) | (±190) | (±106) | (±67) |
| E. coli | 140,000 | 11,000 | 2,700 | 559 | 270 | 101 | 52 |
| | | (±3,100) | (±250) | (±90) | (±50) | (±35) | (±30) |
| C. albicans | 112,000 | 12,400 | 2,840 | 960 | 388 | 192 | 118 |
| | | (±1,100) | (±230) | (±80) | (±28) | (±36) | (±52) |

[Experimental example 2: Test for killing mites]

Mites used for test was the house dust mites (samples containing *Dermatophagoides farinae*, *Dermatophagoides pterohyssinus* and *Tyrophagus putrescentiae* mixed up one another were used) which were generally known as primary cause of allergy, which was distributed from the parasitology class of the medical college of Yonsei University in Korea. After the opening the lid of the tube containing twenty mites, the mites were exposed to the environment with the ozone of 50 ppm and the humidity of 72% for 2 hours while the mites were not exposed directly to the ultraviolet rays. After exposition of the mites to the ozone for a given time period, foldable cover from a folded condition into a developed condition in which the foldable cover defines the sterilizing and disinfecting room.

4. An apparatus comprising: a cover defining a sterilizing and disinfecting room, said cover including an open area for accessing the sterilizing and disinfecting room and means for opening and closing said open area, the open area being sized and configured for introducing bedclothes into the sterilizing and disinfecting room; and a generator for generating ultraviolet rays and ozone, and directing the ultraviolet rays and ozone into the sterilizing and disinfecting room, the generator having a compartment formed therein and a lid for closing the compartment, the cover being attached to the compartment and foldable for accommodation in the compartment.

5. The apparatus as claimed in claim 4, wherein said means for opening and closing said open area comprises a zipper adapted to close the open area to prevent outflow of ozone.

6. The apparatus as claimed in claims 4, wherein said cover is made of a plastic film which is sealed hermetically to prevent outflow of the ozone.

7. The apparatus as claimed in claim 4, wherein said cover is made of a foldable coated fabric sheet which is sealed hermetically to prevent outflow of the ozone.

8. The apparatus of claim 7, wherein the cover includes a coating which prevents outflow of the ozone.

9. The apparatus as claimed in claim 4, wherein said generator for generating ultraviolet rays and ozone includes a stay for maintaining the space on the inside of said sterilizing and disinfecting room.

10. The apparatus as claimed in claim 4, further comprising a support for bedclothes placed in said sterilizing and disinfecting room, said support allowing multidirectional ozone access to said bedclothes.

11. The apparatus as claimed in claim 10, further comprising a reflection mirror which irradiates the ultraviolet rays to said bedclothes when said bedclothes are placed on said support.

12. The apparatus as claimed in claim 4, wherein said generator for generating ultraviolet rays and ozone includes a fan for circulating the ozone in said sterilizing and disinfecting room.

13. The apparatus as claimed in claim 4, wherein said means for opening and closing said open area comprises a fastening string adapted to close the open area to prevent outflow of ozone.

14. The apparatus of claim 4, wherein bedclothes are isolated in the sterilizing and disinfecting room.

* * * * *